(12) United States Patent
Hughes et al.

(10) Patent No.: US 6,877,271 B2
(45) Date of Patent: Apr. 12, 2005

(54) METHOD AND APPARATUS FOR DISPERSING A VOLATILE COMPOSITION

(75) Inventors: John Farrell Hughes, Southampton (GB); Rodney Thomas Fox, Cottingham (GB); Jennifer Jane Knapp, Southampton (GB); Neale Mark Harrison, Burton-on-Trent (GB); Lindsey Faye Whitmore, Winchester (GB)

(73) Assignees: Reckitt Benckiser (UK) Limited, Slough (GB); University of Southampton, Southampton (GB)

( * ) Notice: Subject to any disclaimer, the term of this patent is extended or adjusted under 35 U.S.C. 154(b) by 26 days.

(21) Appl. No.: 10/774,475

(22) Filed: Feb. 10, 2004

(65) Prior Publication Data

US 2004/0154214 A1 Aug. 12, 2004

Related U.S. Application Data

(62) Division of application No. 09/868,125, filed on Sep. 25, 2001, now Pat. No. 6,701,663.

(30) Foreign Application Priority Data

Dec. 24, 1998 (GB) .............................................. 9828728
Jan. 19, 1999 (GB) .............................................. 9901146

(51) Int. Cl.[7] ............................................ A01M 13/00
(52) U.S. Cl. ....................................... 43/124; 43/132.1
(58) Field of Search ...................... 43/124, 125, 132.1; 361/225, 226, 230, 231, 232

(56) References Cited

U.S. PATENT DOCUMENTS

| | | | | |
|---|---|---|---|---|
| 3,638,058 A | * | 1/1972 | Fritzius | 313/359.1 |
| 3,751,715 A | * | 8/1973 | Edwards | 361/230 |
| 4,231,766 A | * | 11/1980 | Spurgin | 96/79 |
| 4,476,515 A | * | 10/1984 | Coffee | 361/226 |
| 4,587,129 A | * | 5/1986 | Kliment | 426/534 |
| 4,735,358 A | * | 4/1988 | Morita et al. | 239/1 |
| 5,024,685 A | * | 6/1991 | Torok et al. | 96/43 |
| 5,077,500 A | | 12/1991 | Török et al. | 315/111.91 |
| 5,180,404 A | * | 1/1993 | Loreth et al. | 96/56 |
| 5,215,558 A | * | 6/1993 | Moon | 96/62 |
| 5,468,497 A | * | 11/1995 | Katsuda | 424/405 |
| 5,653,052 A | * | 8/1997 | .O slashed.stlie | 43/17.1 |
| 5,749,520 A | | 5/1998 | Martin et al. | 239/44 |
| 6,032,406 A | * | 3/2000 | Howse et al. | 43/114 |

FOREIGN PATENT DOCUMENTS

| | | | |
|---|---|---|---|
| FR | 2067959 | 8/1971 | ............ A01N/9/00 |
| GB | 615.332 | 1/1949 | |
| GB | 2066076 | 7/1981 | ............ A61L/2/14 |
| RU | 1803671 | 3/1993 | ............ F24F/3/00 |
| WO | WO92/15339 | 9/1992 | ............ A61L/9/12 |
| WO | WO96/33539 | 10/1996 | ............ H01T/23/00 |
| WO | WO97/01273 | 1/1997 | ............ A01M/1/22 |

OTHER PUBLICATIONS

Copy of GB Search Report for GB 9901146.2 dated Feb. 26, 1999.
Copy of GB Search Report for GB 9828728.7 dated Feb. 26, 1999.
Copy of PCT Search Report for PCT/GB99/04312 dated Mar. 27, 2000.

\* cited by examiner

Primary Examiner—Teri P. Luu
Assistant Examiner—T. Nguyen
(74) Attorney, Agent, or Firm—Fish & Richardson P.C.

(57) ABSTRACT

An apparatus and method for dispersing a volatile composition, which method comprises dispersing the volatile composition into an air steam; and generating an ion wind, thereby causing the molecules of the composition to become electrically charged. The composition can be an insect repellent, an insecticide, an anti-microbial, an anti-allergenic or a room-fragrancing composition

7 Claims, 2 Drawing Sheets

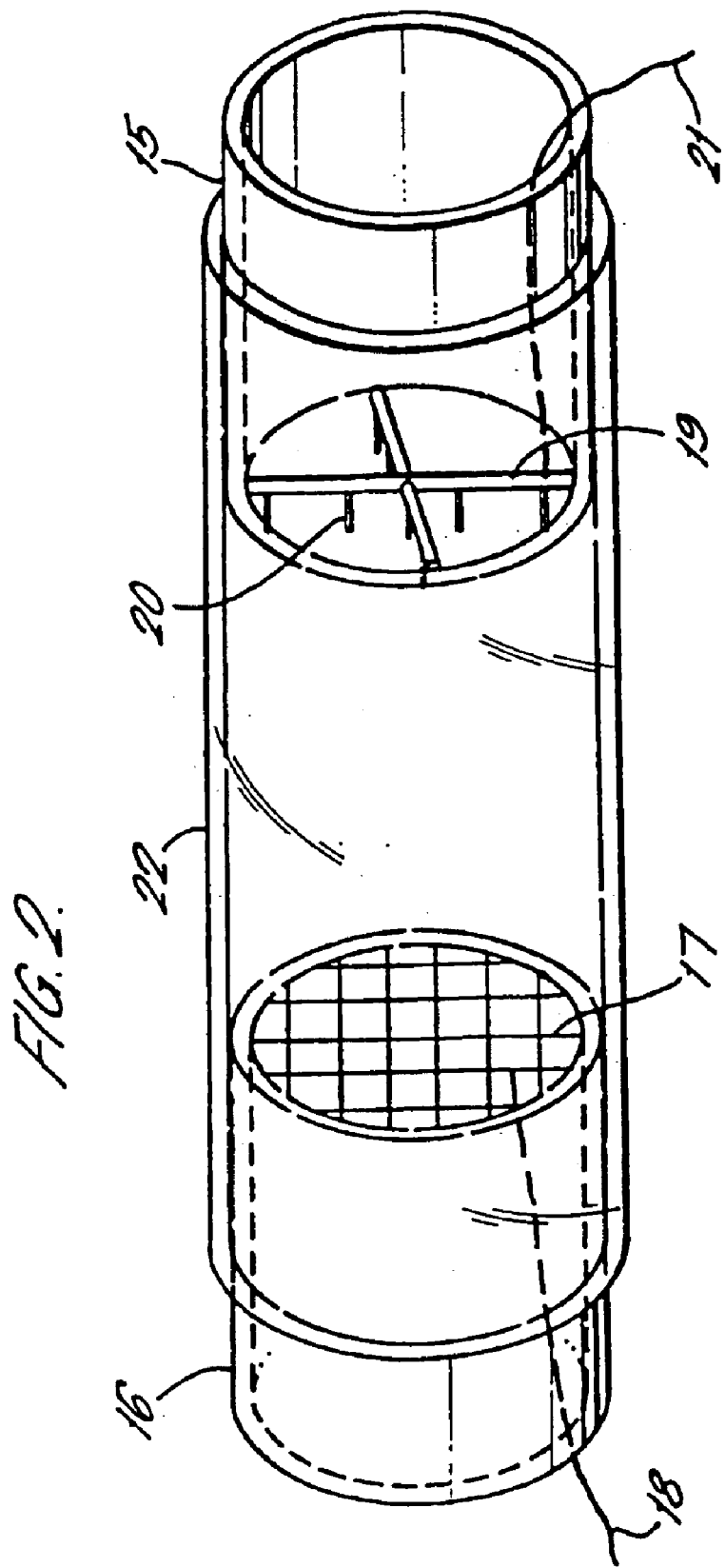

METHOD AND APPARATUS FOR DISPERSING A VOLATILE COMPOSITION

This application is a Div of Ser. No. 09/868,125 filed Sep. 25, 2001 U.S. Pat. No. 6,701,663

BACKGROUND OF THE INVENTION

The present invention relates to a method and apparatus for dispersing a volatile composition into the air and, in particular, to a method and apparatus which relies upon an ion wind to facilitate the dispersal into the air of one or more volatile compounds from a source of a volatile composition.

Compositions which are frequently dispersed into the air include insect repellents, insecticides and air freshening or room fragrancing compositions.

Chemical insect repellents are known in the art and are widely used. For example, N,N-diethyl-m-toluamide (DEET) is widely used as an insect repellent for use on clothing and the skin to repel insects which bite, such as mosquitoes. Citronella oil and eucalyptus oil are also used for the same purpose. However, the application of such chemicals has disadvantages in that they need to be frequently reapplied and they can produce allergic responses in some people.

Pesticides, such as synthetic pyrethroids also have a repellent and/or insecticidal action and can be used to treat clothing, mosquito nets etc. However, prolonged or frequent exposure to synthetic insecticides may be hazardous to health.

Alternatively, insects can be excluded from contact with human beings by providing physical barriers, such as netting or fly screens, over windows and doors, or mosquito netting around beds. The disadvantage of such physical barriers is that the entry of air is severely restricted when the barriers are in place because of the small mesh size required to exclude the insects. This leads to discomfort in hot climates.

Another alternative for use in enclosed spaces, particularly for use overnight, is to burn an insect coil for example containing an insecticidal composition containing a pyrethroid active agent which may also have a repellent effect. Alternatively, an electrical device may be used in which insecticidal tablets containing an insecticidal composition such as a pyrethroid active agent which may also have a repellent effect are heated electrically so that the insecticide/repellent evaporates into the air space and repels and/or kills insects, in particular mosquitoes.

Ultrasound devices have also been sold for repelling mosquitoes, but their efficacy has not been scientifically proven.

Various methods are known for the dispersion of fragrance compositions, such as air fresheners, into a space. For example, an aerosol device may be used to dispense an aerosol spray of the fragrance composition. A disadvantage of such devices is that the fragrance generally only has an effect within the direction of the line of spray and does not last for very long. Other methods of delivering fragrance composition into a space include:

(a) natural evaporation of a liquid fragrance composition delivered to, and exposed to, the atmosphere by means of a porous wick;
(b) natural evaporation and decomposition of a solid gel which includes the fragrance composition; and
(c) enhanced evaporation of a liquid fragrance composition by local heating of a wick delivery system.

In general, these methods simply distribute a fragrance within an enclosed environment, the sole purpose being to create a perfumed atmosphere.

Ion winds are known in the art and an ion wind is generated as a direct result of the interaction between negatively or positively charged ions and air molecules. Ion winds are described and explained in "Electrostatics: Principles, Problems and Applications", J. A. Cross, 1987, Adam Hilger, pp 278–284.

Ion winds may be generated using an electrode arrangement in which a first electrode has one or more sharp points and a second electrode acts as an opposing electrode. If the electric field at the tip of the sharp point or points of the first electrode exceeds the breakdown field of air (approximately 30 kV/cm) then electrical breakdown of the air will occur for either an ac or dc potential applied to the electrode. This phenomenon is generally termed "corona discharge".

For a dc potential, ions which are of opposite polarity to that of the first electrode will be attracted to the first electrode and collected. Ions of the same polarity to that of the first electrode will be repelled by it, and will be attracted towards the second electrode. The ions are of approximately the same size as neutral air molecules and since the ions which are attracted to the second electrode are under the influence of an electrical field (E), a force of $F=qE$ will be exerted on them which causes the air molecules to move. As the ions move, they collide with neutral air molecules and momentum sharing occurs. This in turn imparts a force on the neutral air molecules thus inducing movement in the same direction. This is known as the "ion-drag" effect and is the mechanism which leads to the bulk movement of air, otherwise termed an "ion wind". Unidirectional airflow will be induced in this way both for +ve and −ve dc potentials.

In an alternating field (ac) ionisation will still occur but there will be no net movement of ions in one direction and thus no ion wind generation.

GB-A-2066076 describes an apparatus in which both positive and negative ionic species are generated using a plasma which is generated using radio-frequency methods.

WO92/15339 describes an apparatus in which an electrostatic charge is applied to a wick system. This results in the formation of a "Taylor" cone at the extremity of the fibres of the wick which causes' atomisation of the liquid from the wick.

SU-A-1803679 describes the use of an electrically driven fan to blow ionized air over a pine tree in order to disperse vapours from the tree into the air.

None of the prior art devices results in a unidirectional induced airflow arising from momentum transfer and hence there is no ion wind produced in the prior art for product dispersion.

We have now developed a method and apparatus using an ion wind whereby a volatile composition may be more effectively distributed throughout a particular space.

SUMMARY OF THE INVENTION

Accordingly, in a first aspect the present invention provides a method of dispersing a volatile insect repellant, insecticide, anti-microbial or anti-allergenic composition which method comprises:

dispersing the insect repellant, insecticide, anti-microbial or anti-allergenic composition into Pan air stream;
and generating an ion wind, thus causing the molecules of the insect repellant, insecticide, anti-microbial or anti-allergenic composition to become electrically charged.

In a second aspect the present invention provides an apparatus for dispersing a volatile composition into the atmosphere, which apparatus comprises:

a housing of an electrically insulating material which is in communication with the atmosphere outside the housing, the housing containing:

(i) a source of a volatile composition; and (ii) means for generating an ion wind comprising a first electrode and a second electrode spaced therefrom to define a region there between such that when a dc electrical potential is applied across the first and second electrodes an electrical field is created in the said region, the ion wind facilitating the dispersal of the source of the volatile composition into the atmosphere and causing the molecules of the volatile composition to become charged, the source of the volatile composition being disposed in the housing downstream of the first and second electrodes.

BRIEF DESCRIPTION OF THE DRAWING

FIG. 2 shows a schematic representation of an ion wind generating device with adjustable electrodes.

DETAILED DISCLOSURE

Figure 1:
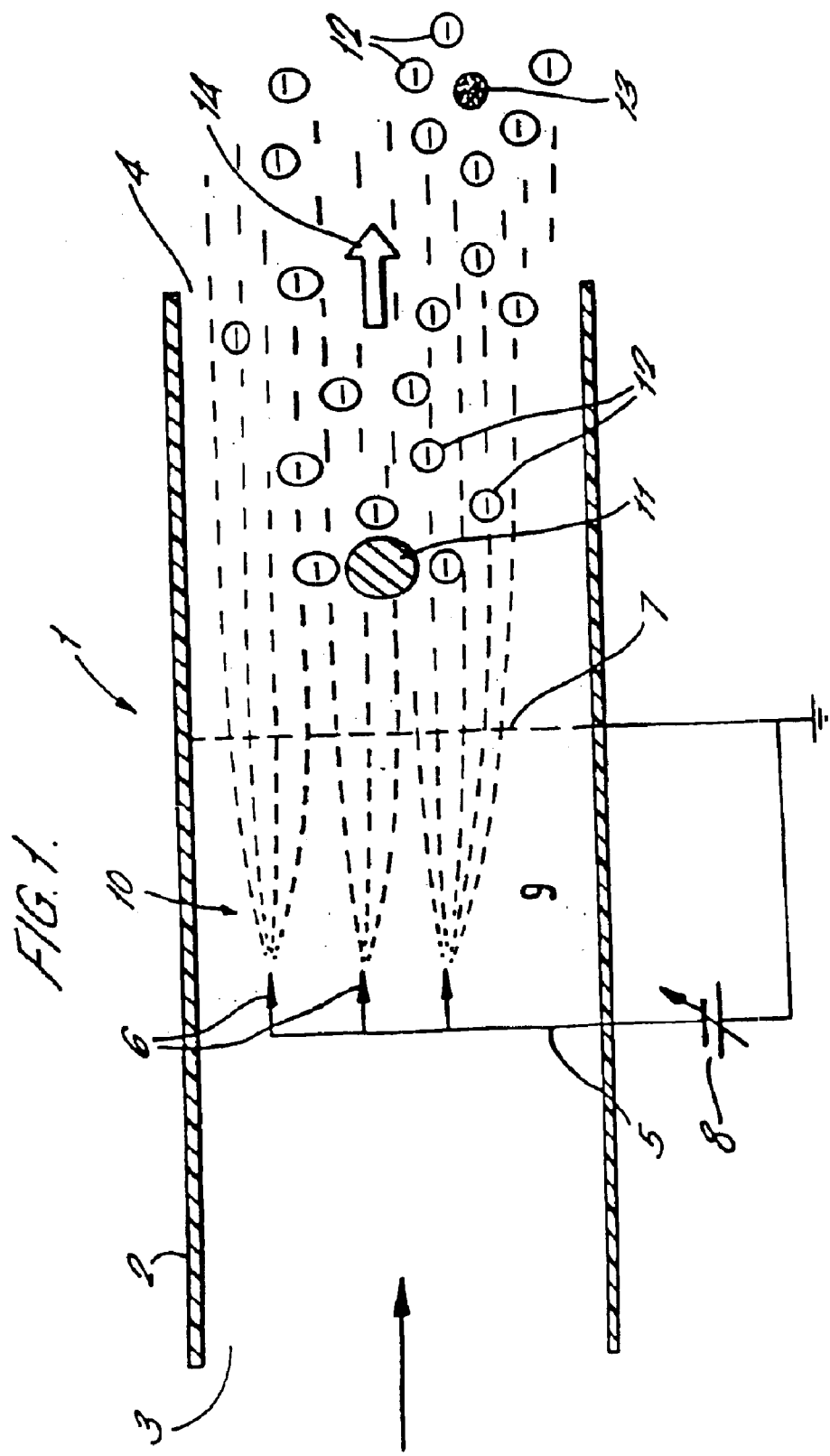
FIG. 1 shows a sectional drawing of one embodiment of the insect repellent device of the present invention.

The present invention uses an ion wind which generates an ionized air flow to facilitate evaporation and dispersal of the volatile composition into the air. A unipolar charge will be transferred to individual molecules of the composition which is evaporated. The composition must be sufficiently volatile, optionally with the assistance of heat, that it can be dispersed into the ion wind air stream. The volatile composition will generally comprise one or more organic molecules. The ion wind not only facilitates the evaporation and dispersal of the volatile composition but also has the added advantages that the ion wind generating device has no moving parts and thus operates at very low noise levels. The ion wind thus acts as an essentially silent fan.

When the composition is vaporized, the unipolar charge will be transferred to any airborne dust particles, allergens, pollen, tobacco particles, microorganisms such as bacteria, viruses and fungal spores, which the vaporized molecules may encounter. Thus, the method of the present invention not, only distributes the composition more effectively, but also enhances the removal of airborne particulates. This is because the air ions generated by the ion wind device attach to particles, such as dust particles as a result of collision and electrostatic attraction. The particles thus charged repel each other due to space charge effects, so reaching surfaces more rapidly than uncharged particles. In close proximity to surfaces (particularly grounded surfaces) the charged particles will be attracted to the surface by image charge attraction. In this way charged particles are precipitated from the air faster than uncharged particles.

The second electrode preferably has at least one opening therein through which the interior of the housing communicates with the atmosphere outside the housing.

In order to generate an ion wind the first electrode has at least one sharp edge or point, for example needle-points, pin-points or razor blades. The second electrode is preferably a ring electrode, a tubular electrode, a grid electrode or a combination of one or more thereof. Generally, the second electrode will be earthed.

When the volatile composition is an insect repellent or insecticide, the insect repellent or insecticidal source which is used will comprise a volatile insect repellent and/or insecticide which is chosen for its repellency and/or toxicity to certain target insect species. For example, insects which it is generally desired to repel include mosquitoes, flies, midges and gnats and in particular those species of these insects which are known to carry disease.

Naturally occurring or synthetic chemicals or chemical compositions which have a repellent effect on certain species of insects include eucalyptus oil, geranium oil, geraniol, pine oil, citronella, neem, thyme oil, thymol, camphor, citronelol, citronelal, linalool, carene, myrcene, terpinene, limnolene, cymene, citronellyl formate, geranyl formate, rose oxide, 2-alkyl-N-acetyloxazolidine, N-acetyl-2-alkyl-4,4-dimethyloxazolidine, dipropyl pyridine-2,5-dicarboxylate, sec-butyl-2-(2-hydroxyethyl)-1-piperidine carboxylate, and methylnaphthalene. Citronella, neem and camphor also have an insecticidal action against some insect species.

Insecticidal compositions, which may also have a repellent action, include pyrethrum and the pyrethroid ester insecticides, including allethrin, bioallethrin, deltamethrin, permethrin and transfluthrin.

The choice of particular repellent or insecticide for use in the present invention will be within the general knowledge of those skilled in this field. Reference may be made to Tomlin C. D. S. (1997) The Pesticide Manual, A World Compendium, BCPC, 11th Edition, 1400 pp, or Brown M. & Herbert A. A. (1997) Insect repellents: an overview. J. Am. Acad. Dermatol. 36, 243–249.

Volatile liquids can also be dispersed which have activity in the air or on surfaces. Because the volatile molecules become charged by the ion-wind, they are attracted to surfaces pina room, and coat them. If the volatile liquid has anti-microbial activity micro-organisms on the surfaces can be counteracted. If the volatile liquid has allergen denaturing properties, allergenic particles on the surfaces can be neutralised.

If the volatile liquid has anti-microbial activity, collision of the charged volatile molecules with micro-organisms in the air can result in the. counteraction of the micro-organisms.

If the volatile liquid has allergen denaturing properties collision of the charged volatile molecules with allergenic particles in the air can result in the neutralisation of the allergen.

When the volatile composition is a fragrance composition, the fragrance source which is used will comprise a volatile composition comprising one or more fragrant components.

Examples of such fragrance components are diethylpthalate, orange terpenes (limonene), styrallyl acetate ester, Cyclacet, methyl ionone ketone, vanillin, Litsea Cybeba, 2-phenylethan-1-ol, dipropylene glycol and methyl-p-3°-butyl hydrocinnamyl aldehyde.

The volatile composition is dispersed into the ion wind stream over a period of time. In order to provide a reasonably constant release of the volatile composition into the ion wind stream the chemicals are generally provided in the form of slow release formulations which may take any desired form. Examples of suitable slow release formulations include the following devices which are impregnated with the desired chemicals: wick or pads of cotton or a synthetic material fed from a reservoir of the composition, gels, rubber septums or strips, membranes, polyethylene vials with or without apertures, microcapsules, polymer beads, solid polymer dispensers, hollow fibres, trilaminate ribbons or extruded polymers. Other systems would include pulsed spray systems and heated evaporators.

When the volatile composition is provided in the form of a gel, the gel will typically comprise carrageenan, water, a volatile component and an emulsifier. When the volatile composition is provided as a liquid providing reservoir for a wick or pad in contact therewith, the liquid will generally comprise volatile component alone, a volatile component and a solvent, a volatile component, a surfactant and water, or a volatile component, surfactant, water and a solvent. It will be understood that mixtures of volatile components may be used, as desired.

The slow release formulation will be chosen to provide the release of the composition over the desired period of time. For example, when the composition is an insect repellent for the repulsion of mosquitoes the device should provide a minimum of at least 8 hours release of the repellent, preferably from 10 to 12 hours. However, longer duration formulations are contemplated within the scope of the present invention which could provide release of the repellent/insecticide over a period of say one week or one month. In such situations the device would include a timer or other activation mechanism to prevent the chemical being released when it was not required, e.g. during daylight hours.

It will be understood that to obtain the desired level of volatile compounds in a room the nature of the composition, in particular the rate of evaporation of the volatile components of the composition, will need to be carefully selected. Furthermore, the ion wind speed needs to be appropriately selected, higher ion wind speeds providing faster evaporation of the volatile components. In addition, the surface area across which the volatile composition is evaporated is also important in determining the rate of evaporation, i.e. the surface area will need to be adapted to the air flow speed.

The apparatus of the present invention may be constructed as a device which is directly plugged into an electrical mains socket, or as a device with an electrical lead enabling it to be positioned where desired within a room, for example clipped onto a bed headrest or positioned on a bedside table. Because the ion wind has a momentum, the charged ions are less likely to be collected on a wall when the device is plugged into an electrical mains socket. Alternatively, the device may be designed to fit into a light bulb socket, a motor vehicle lighter socket, or may be a free-standing battery powered device which could be positioned anywhere within a room or tent or vehicle.

The source of the volatile composition is disposed in the housing downstream of the first and second electrodes.

Whilst an ion wind generating device has some effect alone in repelling insects, i.e. charged air molecules have some effect in repelling insects, the addition of a volatile insect repellent to the ionised air stream significantly enhances this repellent effect.

The present invention will be further described with reference to the accompanying drawings.

Referring to FIG. 1, the apparatus 1 comprises a housing 2 of a substantially insulating material, such as glass or plastic. The housing 2 has openings 3 and 4 at either end thereof in communication with the atmosphere.

Protruding into the housing is a first electrode 5, which is electrically conducting and which has a plurality of pointed tips 6. The electrode is insulated from the housing by suitable means not shown. A second electrically conducting earthed electrode 7 in the form of a screen or mesh is contained within the housing and spaced from electrode 5.

When a dc electrical potential from a source 8 of 5 to 20 kV, depending upon the spacing between electrodes 5 and 7, is applied to the first 5 or second 7 electrodes, the potential difference between these electrodes results in an electrical field 9 in the space 10 between the electrodes. When the electrical field 9 between the first 5 and second 7 electrodes is sufficiently strong, atoms and molecules in the atmosphere in the region near the tips 6 of the electrode 5 become ionized. Ions of opposite polarity to electrode 5 are subsequently repelled from electrode 5 to the second electrode 7. This flow of ions in an electric field gives rise to an induced air flow termed an "ion wind" and is represented in FIG. 1 by the plurality of negatively charged ions.

A slow release source of a volatile composition 11 is positioned downstream of the second electrode. As the ionized air passes over the source 11, molecules of the composition are vaporized by the air stream and become charged by means of the ionized air. The charged molecules of the composition are illustrated at 12. As shown schematically in FIG. 1 the charged molecules 12 of the volatile composition will be attracted to any body 13 in the air due to the configuration of the electric field in close proximity to the body 13. When the volatile source is an insect repellent, the charged molecules will be attracted to insects. When the volatile source is a fragrance composition, the charged molecules will be attracted to particles, such as dust particles, in the air.

The overall effect of the apparatus of FIG. 1 is that an induced ion wind shown by arrow 14 is generated by the device which carries charged particles of the volatile composition.

Furthermore, not only will the charged molecules of the volatile composition be attracted to insects, or particles in the air, e.g. dust, tobacco particles, allergens or microorganisms, but they will also be attracted to any other surfaces such as bedding, furniture or even human beings which act as grounded targets.

Referring to FIG. 2, an ion wind generating device was constructed from two plastic tubes 15, 16 measuring 50 mm in diameter and 50 mm in length. The first tube 15 has a metal grid 17 covering one end thereof, with the spacings between the wires of the grid being 6 mm. The grid was earthed via a suitable wire connection 18. Inside the second tube, 16, was placed the corona electrode 19 which comprised a cross formation comprising aluminium strips holding tufts of stainless steel brushes 20. Each arm of the cross comprised four tufts of brushes, 12 mm apart. The electrode 18 was connected to a voltage source via a cable 21. The two plastic tubes 15, 16 were held together with a cylinder of transparent plastics material 22 along the inside of which the two tubes 15, 16 could be slid. In this way the spacing between the earthed grid 17 and the corona electrode 18 could be varied. A voltage of 10 kV was applied from a power supply at a current not exceeding 200 $\mu$A.

Using this device an ion wind airflow of 1.0 m/second was achieved by setting the interelectrode distance to 12 mm. To obtain an ion wind airflow of 0.5 m/second a spacing of 25 mm between the electrode was required.

Although the method and apparatus of the present invention in relation to insect repellents and insecticides have been described above mainly in relation to their use against biting insects, such as mosquitoes, other uses could include:

- the delivery of insect repellents and/or insecticides to counter insect pests in storerooms, warehouses, granaries and silos;
- the delivery of insect repellents and/or insecticides to counter insect pests in animal houses, such as stables or animal rearing units; and
- the delivery of insect repellents and/or insecticides to counter pests which attack natural fibres, such as moths.

The advantages of the use of an ion wind to disperse insect repellents are twofold. First, the device acts as simple fan, so that the volatile repellent substance is dispersed quickly. Secondly, the molecules of the repellent show enhanced targeting. This occurs because the stream of charged ions produced by the device confers a charge to the volatile repellent molecules, thereby producing charged repellent molecules. Contact with the insects themselves, any surfaces the insects touch, including the animal host, is thus enhanced. This may result in a reduction in the number of flights, landings and bites by the insects.

An additional advantage is that less repellent may be required to achieve the same, or even greater effect, because of the enhanced targeting.

The method and apparatus of the present invention when used for dispersing a fragrance composition provide an enhanced distribution of the fragrance composition within a space, as compared to other known methods. As the plume of the fragrance composition carries a unipolar charge, the molecules will interact with any particle in the atmosphere leading to an enhanced clearing of the air because the dust or other particles become indirectly charged and precipitate due to mutual repulsion.

Furthermore, because the molecules of the fragrance composition carry a unipolar charge, these molecules will be attracted to the human body and face, thereby giving an enhanced fragrance effect to a person in the vicinity of the apparatus. Additionally, there will also be a longer lasting fragrance effect due to the result of the deposition of the fragrance composition in the nasal region of a person in the vicinity of the apparatus. These effects are achieved because the molecules of the fragrance composition will seek to disperse as a result of mutual repulsion and will preferentially move towards grounded surfaces.

The present invention will be further described with reference to the following Examples.

EXAMPLE 1

The ion wind generating device as described with reference to FIG. 2 was used to generate an ion wind airflow of 0.5 m/second with a spacing of 25 mm between the electrodes.

With an ion wind travelling at 0.5 m/second; 1.45 g of a fragrance (Lavender & Camomile F537.956 ex Quest) was evaporated over a 24 hour period from a polyether sleeved wick in communication with a source of the fragrance. Sensory tests showed that this amount of evaporation corresponds to an appropriate strength of fragrance to perfume a room approximately 16 metres square. Lower ion wind speeds will give lower levels of perfume delivery and higher ion wind speeds higher levels of perfume delivery.

EXAMPLE 2

The Bioelectrostatics Research Centre of the University of Southampton developed a new protocol to test the use of an ion wind to disperse an insect repellent. A specially constructed test room was used as the test chamber. The door of the room was modified, so that it had a rectangular hole, measuring 62.5 cm×62.5 cm at the base. Two circular holes measuring 10 cm were cut in the door at 141 cm and 65 cm from the ground. The lower shelf was used to hold an ion wind generating device in position during the test. The ion wind generating device was constructed from a 6 mm thick Perspex tube (100 mm external diameter) in which the electrodes were housed. The high voltage electrode was a seven pin brass electrode, whilst the other electrode was a coiled electrode made of brass. The device was otherwise constructed and connected in an manner identical to that described with reference to FIG. 1. A small shelf was constructed just below the hole to allow a glass vial containing the repellent compound to be positioned in such a way that evaporating molecules would be picked up by the ion wind stream. The upper hole allowed visual access to the room and acted as an entry point for the mosquitoes. Tubegauz was attached around the holes on the outside of the door to prevent any escapes.

The interior of the room contained a large cage constructed of narrow metal girders (Dexion). This measured 183×62.5×62.5 cm. This cage was covered with lining paper on four sides. The base of the cage and one end were left open. Masking tape was used to secure the paper to the cage. An opening (21×29.5) cm was cut in the top of the paper 16 cm from the closed end. A piece of nylon netting was used to cover this. This opening provided a window through which the odour and warmth of the human test subject could escape and attract the mosquitoes. A foam rubber mattress covered with polythene sheeting was placed inside the cage for the comfort of the human test subject.

The cage was closely aligned with the hole in the bottom of the door, so that the gap was continuous with the cage. The cage was then taped to the floor on the outside with making tape. An electric heater maintained the room at 24° C. (+/−2° C.). The room was otherwise empty.

Thirty minutes before the start of each test, fifty female *Aedes aegypti* mosquitoes were placed into the test room. The mosquitoes had previously been fed only on a 50/50 sugar/water mixture, and had not received a blood meal. They had not previously been used in a test.

The human subject entered the cage and lay on the mattress, so that the face of the subject was directly below the opening.

Citronella was released by placing it in a :mall glass vial containing a cotton wick. Each experimental condition was tested for 20 minutes. The human subject was asked to observe the behaviour of the mosquitoes and call out 'land' each time a mosquito landed or the net and 'touch' if this lasted less than a second. Each event was recorded by the experimenter who sat behind the door. Each time a mosquito flew past the subject's field of view it was recorded by the subject with a tally counter. Each twenty minute period was divided into 5 minute periods. The subject was asked every 5 minutes to call out the number of the counter, which was then recorded.

After each test the insects were killed with a fast acting pyrethroid spray. The room was vented for 1 hour before all surfaces in the room were washed with a detergent solution.

Results

TABLE 1

| | Mean number of mosquitoes | |
|---|---|---|
| | touch | landing |
| Human | 68 | 109 |
| Human + ion wind | 5.8 | 17.7 |
| Human + citronella | 10.5 | 27.9 |
| Human + citronella + ion wind | 3.2 | 9.2 |

These results show that the number of contacts made by the mosquitoes is dramatically reduced by the use of the ion wind alone or together with a mosquito repellent.

What is claimed is:

1. An apparatus for dispersing a volatile composition into the atmosphere, which apparatus comprises a housing of an electrically insulating material which is in communication with the atmosphere outside the housing, the housing containing:

a source of a volatile composition; and means for generating an ion wind comprising a first electrode and a second electrode spaced therefrom to define a region therebetween such that, when a dc electrical field is created in said region, the ion wind facilitates the dispersal of the source of the volatile composition into the atmosphere and causes molecules of the volatile composition to become charged, the source of the volatile composition being disposed in the housing downstream of the first and second electrodes.

2. An apparatus as claimed in claim 1 where in the first electrode has at least one sharp edge or point.

3. An apparatus as claimed in claim 2 wherein the second electrode is a ring electrode, a tubular electrode, a grid electrode, or a combination of one or more thereof.

4. An apparatus as claimed in claim 3 wherein the second electrode is earthed.

5. An apparatus as claimed in claim 1 wherein the source of the volatile composition is provided as a slow release formulation.

6. An apparatus as claimed in claim 1 which is adapted to run from an electrical mains supply or light bulb socket.

7. An apparatus as claimed claim 1 which is adapted to run from a battery or a motor vehicle lighter socket.

* * * * *